United States Patent [19]

Hoshowski

[11] Patent Number: 4,764,174

[45] Date of Patent: Aug. 16, 1988

[54] NITROPHENYLENEDIAMINE DYE COMPOSITION HAVING IMPROVED DEPOSITION ON HUMAN HAIR AND WOOL

[75] Inventor: Myra A. Hoshowski, Addison, Ill.

[73] Assignee: Helene Curtis, Inc., Chicago, Ill.

[21] Appl. No.: 824,244

[22] Filed: Jan. 30, 1986

[51] Int. Cl.⁴ .................. A61K 7/13; A61K 7/075; C11D 1/94; C11D 3/40

[52] U.S. Cl. .................................. 8/415; 8/405; 8/406; 252/545; 252/550; 252/DIG. 13; 424/70

[58] Field of Search .................. 8/415, 405, 406; 424/70; 252/DIG. 13, 545, 550

[56] References Cited

U.S. PATENT DOCUMENTS

| | | | |
|---|---|---|---|
| 3,168,442 | 2/1965 | Brunner et al. | 167/88 |
| 4,185,958 | 1/1980 | Bugaut et al. | 8/10.1 |
| 4,329,334 | 5/1982 | Su et al. | 424/70 |
| 4,337,061 | 6/1982 | Bugaut et al. | 8/405 |
| 4,419,101 | 12/1983 | Bugaut et al. | 8/415 |
| 4,470,826 | 9/1984 | Bugaut et al. | 8/115 |

FOREIGN PATENT DOCUMENTS 0137178 4/1985 European Pat. Off. .

OTHER PUBLICATIONS

Harry, Ralph A., *Cosmetic Material*, vol. 2, 1963, pp. 49–50.

*Primary Examiner*—A. Lionel Clingman
*Assistant Examiner*—Linda D. Skaling
*Attorney, Agent, or Firm*—Mason, Kolehmainen, Rathburn & Wyss

[57] ABSTRACT

A nitrophenylenediamine dye composition includes a long chain alkyl (8 to 18 carbon chain length) sulfate detergent, such as sodium lauryl sulfate or ammonium lauryl sulfate together with a sultaine (sulfobetaine) surfactant in a ratio of sulfate/sultaine in the range of 1:1 to 10:1, and particularly in the range of 6:1 to 9:1 to achieve unexpectedly increased deposition of specific nitrophenylenediamine dyes onto human hair.

46 Claims, 4 Drawing Sheets

NITROPHENYLENEDIAMINE DYE COMPOSITION HAVING IMPROVED DEPOSITION ON HUMAN HAIR AND WOOL

FIELD OF THE INVENTION

The present invention relates to a nitrophenylenediamine semi-permanent dye composition achieving new and unexpected deposition of nitrophenylenediamine dyes onto human hair, and to a method of dyeing human hair. More particularly, the present invention is directed to a nitrophenylenediamine dye composition containing a long chain alkyl (8 to 18 carbon chain length) non-ethoxylated sulfate detergent, such as sodium lauryl sulfate or ammonium lauryl sulfate together with a sultaine (sulfobetaine) surfactant in a ratio of sulfate/sultaine in the range of 1:1 to 10:1, and particularly in the range of 6:1 to 9:1 to achieve unexpectedly increased deposition of specific nitrophenylenediamine dyes onto human hair.

BACKGROUND OF THE INVENTION AND PRIOR ART

Nitrophenylenediamine dyes have been in existence since about 1900 and, since then, a great many nitrophenylenediamine dyes have been developed for hair dye compositions, as disclosed in U.S. Pat. Nos. 3,168,442; 4,337,061; 4,419,101 and 4,470,826.

As disclosed in the above-cited United States patents, the nitrophenylenediamine dyes are included in dyeing compositions including one or more anionic, cationic, non-ionic or amphoteric surface-active agents. Further, combinations of anionic and amphoteric detergents are commonly used for non-dye-shampoos as disclosed in the Su et al U.S. Pat. No. 4,329,334 disclosing a combination of an anionic sulfate with a cocoamidopropylsulfobetaine.

The experimental work in the nitrophenylenediamine dye area appears to have been concentrated, for the most part, in the synthesis of new nitrophenylenediamine dye compounds, as evidenced by the above cited U.S. patents. In this regard, there has been much work in Great Britain in the field of synthesis of nitrophenylenediamine dyes for hair dyeing compositions by Unilever, L'Oreal and Clairol as evidenced by the great number of British patents cited in The Chemistry of Synthetic Dyes, Volume 5, copyright 1971 by John S. Corbett, Chapter VII, pages 475–531.

It is well known that common hair shampoos contain an effective and low-to-non-irritating amount of an anionic alkyl sulfate as a principal cleansing agent, plus a number of other formulation ingredients included for product stability and customer acceptance. Likewise, direct dyeing of hair with nonionic dyes is well-known. These dyes, when used alone, work by penetrating the hair shaft without the use of peroxides or other agents. However, the use of elevated temperature heating caps, for rather long periods of time, is required to obtain satisfactory results. Attempts have been made to apply these dyes with various types of anionic surfactants. Early attempts of combining a non-ionic direct dye with a shampoo led to unsatisfactory results due to failure to effectively clean the hair, failure to give satisfactory coloring results, or the need for excessively long hair contact times or high dye concentrations necessary at ambient temperatures. Excess dye led to better coloring effects, but most tended to be rinsed away, or the excess dye stained the skin.

Further, others have investigated the mechanism behind the diffusion of semi-permanent hair dyes, such as the nitrophenylenediamines into human hair fibers, as described in the Journal of The Society of Cosmetic Chemists, Vol. 36, pages 1–16 (January/February 1985), Diffusion Of Semi-permanent Dyestuffs Into Human Hair by S. K. Han, Y. K. Kamath and H. D. Weigmann. As described in this article, the diffusion of $N_1$-(2-hydroxyethyl)-2-nitro-p-phenylenediamine into human hair was investigated and it was concluded that the diffusion or deposition of the nitrophenylenediamine dye was dependent essentially only upon the pH and solvent composition of the dye bath and that the solvent effect was associated with the lower solubility of the nitrophenylenediamine dye in aqueous solution rather than in a 50 volume percent aqueous ethanol bath.

Others have attempted to determine the reasons for a low tinctorial power of other dyes, such as the henna color treatments in which 2-hydroxy-1,4-napthoquinone is the known active color principle, as disclosed in Commercial Premixed Henna Color Treatments and Conditioners, by Dolores Kenney, Cosmetics & Toiletries, Volume 95, June 1980, pages 43–52 and have found that in certain commercial henna-based dye compositions, the low tinctorial power of these commercial highlighting shampoos was attributable to the combination of anionic and amphoteric surfactants resulting in decreased tonal depth thus leading away from any such combination of anionic and amphoteric surfactants in a dye-shampoo composition.

As described in the article, Hair Colouring Shampoos, Soap, Perfume & Cosmetics, Vol. 48, June 1973, pages 357 and 358, betaine detergents have been used in hair coloring shampoos containing a basic dye or a quaternary dye. The betaines have been used with the basic and quaternary dyes since these dyes are incompatible with the most effective shampoo bases, such as the anionic lauryl sulfates. Accordingly, a non-ionic surfactant must be used with the basic and quaternary dyes to achieve compatibility even though such non-ionics are unsatisfactory as shampoo bases since they produce little lather in contact with soiled hair.

One recently published European application (published Apr. 17, 1985, Bulletin 85/16, Publication No. 137,178, Application No. 84109141.6) discloses a hair dye composition useful for increased deposition of nitrophenylene diamine dyes onto human hair, including a combination of surfactants and may include a long chain ether sulfate and a betaine, such as cocoamidopropyl betaine. While this shampoo appears to be effective for increased deposition of nitrophenylenediamine dyes, the lathering and, therefore, cleansing properties are not as good as would be possible if the shampoo were based upon a non-ethoxylated long chain anionic, such as a lauryl sulfate. As well known, as presented by Roger Hart of W. R. Grace & Co. at Cosmo Expo 9, New York, June 24, 1981, FORMULATING IMPROVED LATHER, and in D & Cl, Feburary 1982, pages 34–36, the ethoxylated long chain anionic surfactants, such as the laureth sulfate salts, do not lather as well as the non-ethoxylated long chain anionic surfactants, such as sodium lauryl sulfate and, therefore, do not achieve consumer acceptance. As shown in FIG. 5 of the instant application, however, the combination of a non-ethoxylated long chain anionic sulfate, such as sodium lauryl sulfate, with a betaine, does not achieve increased deposition of nitrophenylene diamine dyes.

Quite surprisingly, in accordance with the present invention, it has been found that the combination of a long chain, non-ethoxylated anionic surfactant, having the formula $CH_2\text{-}CH_{2n+1}OSO_3M$ wherein n=8 to 18 and M is any suitable cation, such as an alkali metal, ammonium, alkyloammonium, or amine together with one or more sultaine surfactants, substantially increases the deposition of nitrophenylene diamine dyes while achieving substantial lathering and, therefore, commercial acceptance.

In accordance with the present invention, new and unexpected lathering and shampooing results are achieved together with new, unexpected and even deposition of one or more nitrophenylenediamine dyes onto human hair at ambient temperature with relatively short contact times using a combination of a nonethoxylated long chain alkyl sulfate and a sultaine.

SUMMARY OF THE INVENTION

In brief, it has been found that a mixture of an anionic long chain alkyl sulfate and an amphoteric sultaine surfactant in a ratio of sulfate/sultaine of 10:1 to 1:1 and especially in a ratio of 6:1 to 9:1 provides new and unexpected and homogeneous deposition of one or more non-ionic nitrophenylenediamine semi-permanent dyes while achieving good cleansing and lathering of human hair or wool.

Therefore, it is an object of the present invention to provide a homogeneous liquid hair dye-shampoo.

It is also an object of the present invention to provide a liquid shampoo capable of both cleansing the hair and coloring the hair in one operation.

Another object of the present invention is to provide a liquid hair dye-shampoo containing a combination of an anionic sulfate surfactant, and an amphoteric sultaine surfactant in a weight ratio of 6:1 to 9:1 anionic/amphoteric to achieve new and unexpected direct color penetration of nitrophenylenediamine dyes into the hair.

Another object of the present invention is to provide a liquid shampoo containing a non-ionic, semi-permanent, direct nitrophenylenediamine dye and a combination of sulfate and sultaine surfactants.

Yet another object of the present invention is to provide an anionic and amphoteric based hair dye-shampoo, containing a nitrophenylenediamine dye, that dramatically and unexpectedly increases penetration of the dye into the hair.

Still another object of the present invention is to provide a nitrophenylenediamine dye-containing anionic and amphoteric-based hair dye-shampoo that will produce a desired color while using less dye and/or reduced contact time of the hair dye-shampoo with the hair.

The above and other objects and advantages of the present invention will become apparent from the following detailed description of the invention taken in conjunction with the drawings, wherein:

DETAILED DESCRIPTION OF THE PREFERRED EMBODIMENTS

Figure 2:
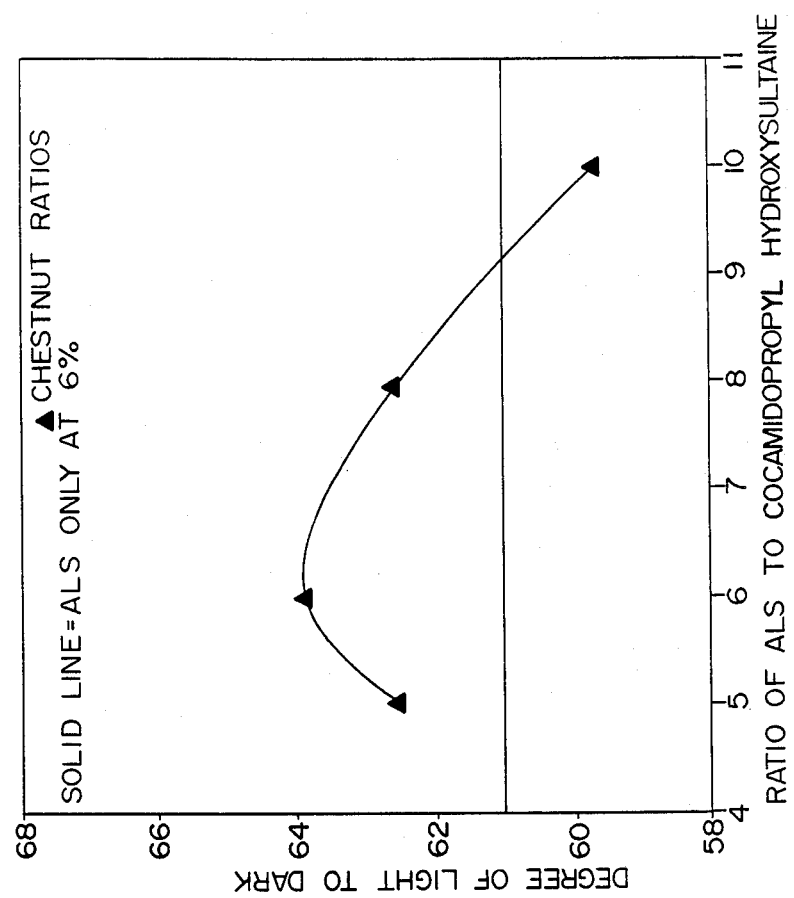
FIGS. 2 and 3 are graphs of the data of Tables 1 and 2, respectively, showing color deposition from dye compositions containing ammonium lauryl sulfate surfactants at 6% by weight and 12% by weight, respectively.

The hair dye composition of the present invention comprises a liquid anionic-amphoteric based hair dye-shampoo, containing one or more nitrophenylenediamines as a semi-permanent direct dye.

The nitrophenylenediamine dyes can be any falling within the following structural formulas (I) or (II):

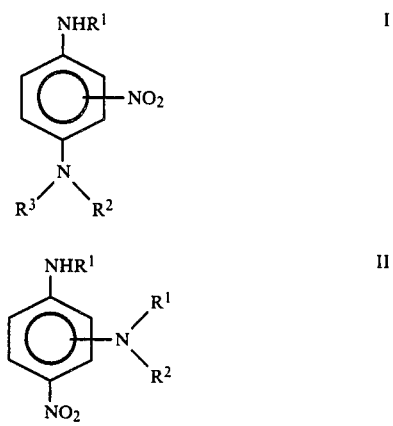

where $R^1$, $R^2$, and $R^3$ are the same or different, consisting of hydrogen, methyl, substitued-methyl, ethyl, substituted-ethyl, propyl or substituted propyl moieties. In the first illustrated structural formula (I) the position of the nitro group varies between the ortho and meta position depending on the color desired. In the second illustrated structural formula (II) the $NR^1R^2$ group varies between the ortho and meta position.

Particularly advantageous nitrophenylenediamine dyes falling within the above two structural formulas are those where $R^1$ or $R^2$ is a monohydroxy alkyl (methyl ethyl or propyl) or a polyhydroxy alkyl (methyl, ethyl or propyl) radical or an aminoalkyl radical, the amino group of which can be mono or disubstituted by an alkyl ($C_{1-3}$) radical.

Particularly suitable examples of nitrophenylenediamine dyes that can be used alone or in combination to produce a desired color and shade, are as follows:

| SEMI-PERMANENT DYES | | |
|---|---|---|
| HC YELLOW #5 | 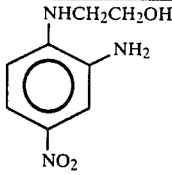 | N—(2-Hydroxyethyl)-4-nitro-o-phenylenediamine |
| HC RED #3 |  | $N^4$—(2-hydroxyethyl)-2-nitro-p-phenylenediamine |
| VIOLET | 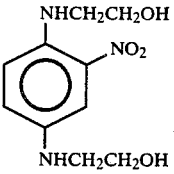 | $N^1,N^4$—bis-(2-hydroxyethyl)-2-nitro-p-phenylenediamine |
| HC BLUE #2 | 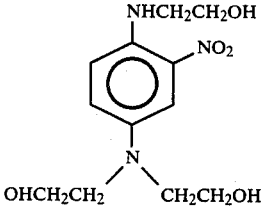 | $N^2,N^4,N^4$—tris-(2-hydroxyethyl)-2-nitro-p-phenylenediamine |
| ORANGE | 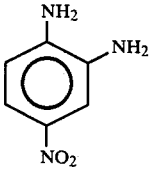 | 4-nitro-o-phenylenediamine |
| YELLOW | 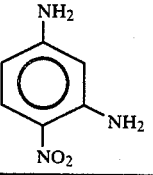 | 4-nitro-m-phenylenediamine |

The nitrophenylenediamine dye should be present in the dye composition in an tinctorially effective amount, for example, at least 0.001% by weight, and preferably at least 0.01%, to as much as needed to achieve a desired color or shade.

The dye composition of the present invention cleanses the hair unexpectedly well while achieving new and unexpected deposition of one or more nitrophenylenediamine dyes onto the hair, at ambient temperatures, in unexpectedly short times. In addition to the nitrophenylenediamine dyes, as defined in a tinctorially effective amount, the composition includes an anionic surfactant, particularly a long chain alkyl sulfate, such as sodium lauryl sulfate or ammonium lauryl sulfate; an amphoteric surfactant, particularly a sultaine, such as cocamidopropylhydroxysulfobetaine; a carrier such as water and/or other solvents; and other optional components, including, but not limited to, alkanolamides, sequestering agents, preservatives, fragrances, thickeners, and the like. As will become more apparent hereinafter, dramatic and unexpected results are obtained with the surfactant combination of an alkyl sulfate and a sultaine, in a nitrophenylenediamine dye composition.

In accordance with an important feature of the present invention, the hair dye-shampoo composition of the present invention includes an anionic surfactant comprising a long chain alkyl sulfate or sulfonate $(C_nH_{2n+1}OSO_3^-M^+)$ wherein $n=8-18$ and M is any suitable cation, such as an alkali metal, ammonium, alkylolammonium, or amine, together with an effective amount of an amphoteric surfactant falling within the formula III or IV:

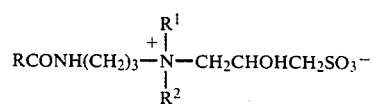

III

-continued
amidosulfobetaine

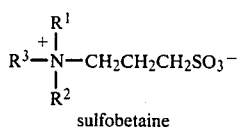

sulfobetaine where R is an alkyl radical containing predominantly 7-17 carbons, $R^1$ and $R^2$ are the same or different alkyl radical having 1-4 carbons, and $R^3$ is an alkyl radical containing predominantly 8-18 carbons.

Figure 1:
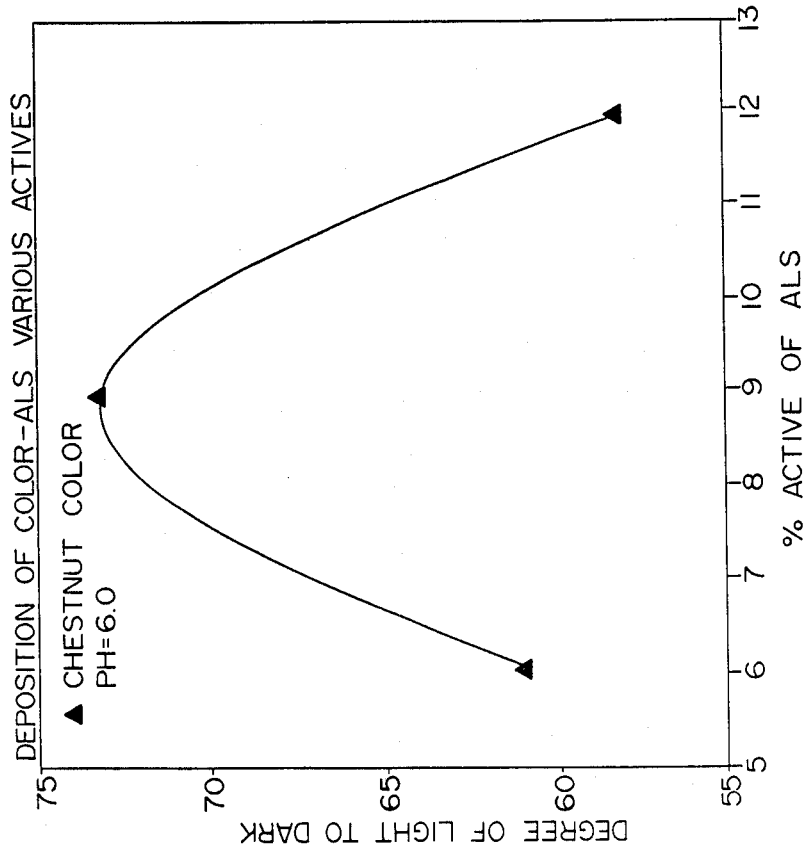
FIG. 1 is a graph of color deposition of the chestnut color of Example 1 onto wool at pH 6.0 showing that the best deposition occurs at an ammonium lauryl sulfate content (without the sultaine) of about 9.0 percent by weight of the dye composition.

To achieve the full advantage of the present invention, the hair dye-shampoo composition of the present invention includes the anionic long chain alkyl sulfate detergent or surfactant in an amount of about 6% to about 12% based on the total weight of the dye-shampoo composition. Best results are achieved when the dye-shampoo composition includes the anionic long chain alkyl sulfate in an amount of 8% to 10% by weight of the composition, and particularly at 8.5 to 9.5% by weight, as shown in FIG. 1.

The anionic alkyl sulfate surfactant provides cleansing and surface activity, and synergistically combines with the sultaine to achieve new and unexpected results and enhanced dye deposition onto human hair and wool. Examples of suitable anionic sulfates in this composition are the water-soluble salts (sodium, ammonium, alkylolammonium) of long chain (predominantly $C_8$-$C_{18}$) synthetic sulfated detergents.

In accordance with another important feature of the present invention, the dye-shampoo composition includes a sultaine falling within the structural formula III or IV in an amount to achieve an anionic alkyl sulfate/sultaine ratio in the range of 1:1 to 10:1 or about 0.5% to 12% and preferably 1% to 8% by weight of the composition. To achieve the full advantage age of the present invention, the ratio of anionic alkyl sulfate/sultaine should fall within the range of about 6:1 to about 9:1. Some nitrophenylenediamine dye compositions exhibit dramatic results in the ratios of 5:1 to 10:1, as apparent from the data in the tables and the drawings, as will be described in more detail hereinafter.

The amphoteric sultaine surfactant provides cleansing, conditioning, and synergistically combines with the long chain alkyl sulfate to achieve new, unexpected and enhanced dye penetration into the hair. In accordance with another important feature of the present invention, the sultaine also conditions the hair to a limited extent.

The pH of the nitrophenylenediamine dye-shampoo composition of the present invention should be in the range of about 3 to about 10 and, to achieve the full advantage of the present invention the pH of the composition should be between about 5 and about 6.5.

The combination of alkyl sulfate and sultaine provides a composition that gives excellent foaming and cleansing of the hair, and achieves unexpected dye deposition in relatively short times. In accordance with additional new and unexpected features and advantages of the present invention, nitrophenylenediamine dyes in the composition do not adversely affect the cleaning ability of the anionic-amphoteric surfactant blend and, because of more rapid deposition or fixing of the dye from the composition of the present invention, the hair can be easily washed and colored in one operation with dye-hair contact times of 40 minutes or less, and particularly in 30 minutes or less. After application of the composition of the invention, the hair should be thoroughly rinsed to remove the excess anionic surfactant from the hair.

The compositions can be thickened with, for example, sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners such as bentonite. These thickeners are preferably present in an amount from 0.5 to 10% by weight and in particular from 0.5 to 3% by weight, relative to the total weight of the composition.

Other common additives may be incorporated with the essential ingredients, as long as the basic properties of the hair dye-shampoo are not adversely affected. These additives include, but are not limited to, commonly used fragrances, opacifiers, pearlescing agents, thickeners, preservatives, sequestering agents, and the like, and will usually be present in weight percentages of less than 1% each, and 2% to 5% in total. The cosmetic vehicle is generally water but it is also possible to add organic solvents to the compositions in order to solubilize compounds which would not be sufficiently soluble in water. Suitable solvents include lower alkanols such as ethanol and isopropanol, polyols such as glycerol, glycols or glycol ethers, such as 2-butoxyethanol, ethylene glycol, ethylene glycol monoethyl ether, propylene glycol and diethylene glycol monoethyl ether monomethyl ether, and mixtures thereof. These solvents may be present in the dye-shampoo composition of the present invention in an amount from 1 to 75% by weight and in particular from 5 to 50% by weight, relative to the total weight of the composition.

In accordance with the present invention, test solutions were prepared with both ammonium and sodium lauryl sulfate to determine the degree of nitrophenylenediamine dye penetration on standard worsted wool, at various pHs between 6 and 7, and it was shown that a 9% by weight lauryl sulfate-nitrophenylenediamine dye solution deposits a chestnut color (Example 1) appreciably better than a 6% or 12% by weight lauryl sulfate-nitrophenylenediamine dye solution (See FIG. 1). The individual lauryl sulfate solutions were then held at 6%, and 12% by weight, and a cocamidopropylhydroxysultaine was added to give solutions having a ratio of anionic to amphoteric surfactants ranging from 5:1 to 10:1, as shown in Table 1 and FIG. 2:

TABLE 1 (FIG. 2)

| Ratio of anionic/ amphoteric | Ammonium Lauryl Sulfate 6% Active Cocamidopropyl Hydroxysultaine Chestnut Color pH = 6.0 | | | | | |
|---|---|---|---|---|---|---|
| | dl Trial 1 | dl Trial 2 | dl Trial 3 | Average | t vs ALS | Significant at 95% ? |
| 1:0 | 61.00 | 61.11 | 61.00 | 61.04 | | |
| 10:1 | 59.72 | 59.51 | 59.42 | 59.55 | 14.58 | Yes* |
| 8:1 | 62.74 | 62.52 | 62.27 | 62.51 | −10.57 | Yes |
| 6:1 | 64.04 | 63.88 | 63.41 | 63.78 | −15.00 | Yes |
| 5:1 | 62.83 | 62.47 | 62.30 | 62.53 | −9.02 | Yes |

*Result significantly lower that with ALS alone

Figure 3:
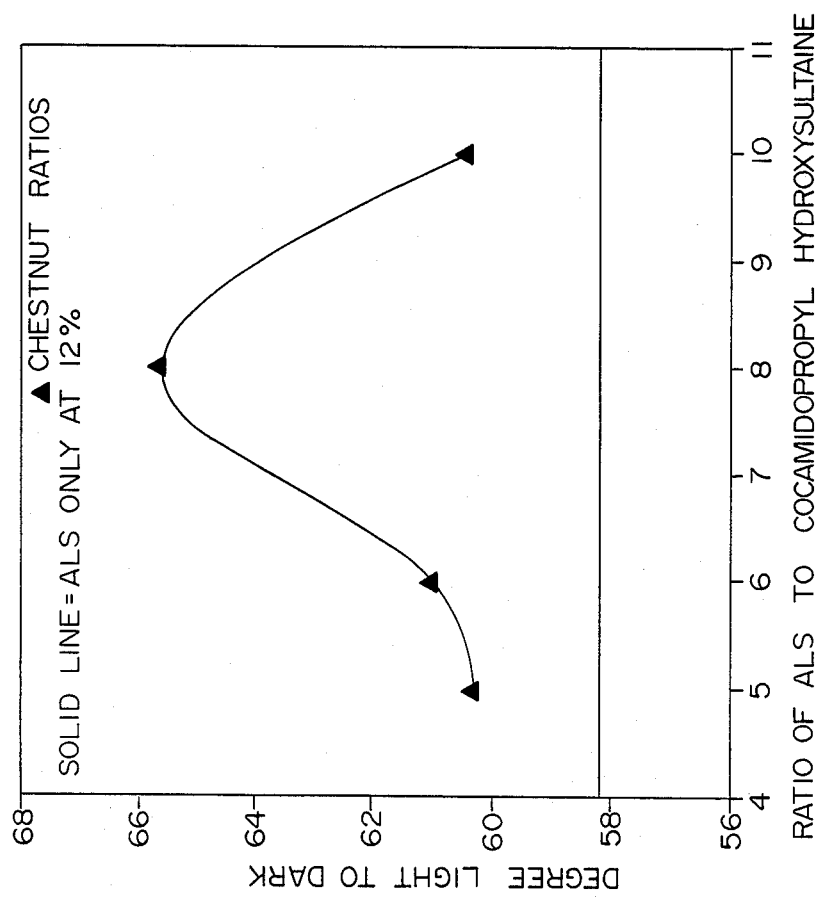
Figure 6:
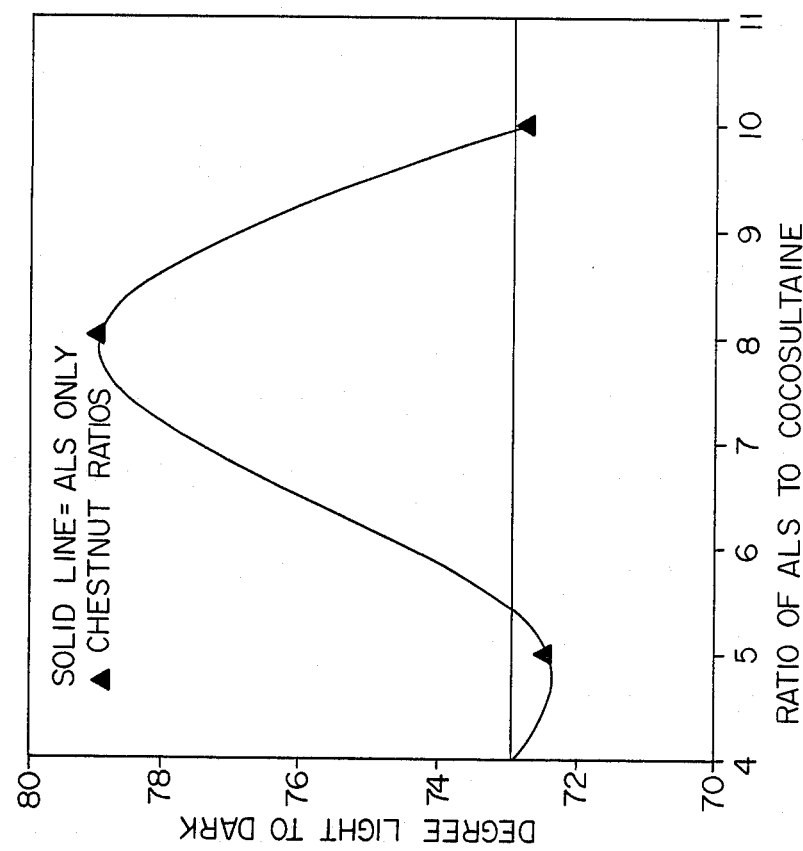

For the 6% lauryl sulfate solution with added sultaine, ratios of anionic/amphoteric of 5:1, 6:1 and 8:1 improved dye deposition over dye deposition using lauryl sulfate alone. At a 10:1 ratio, dye deposition decreased. With the 12% lauryl sulfate solution, all mixed lauryl sulfate/sultaine mixtures gave better dye deposition than lauryl sulfate alone, with the maximum deposition occurring at an 8:1 anionic/amphoteric ratio as shown in Table 2 (FIG. 3). However, overall better dye deposition could be obtained at an anionic loading of about 9%, as shown in FIG. 1

TABLE 2 (FIG. 3)

Ammonium Lauryl Sulfate 12% Active
Cocamidopropyl Hydroxysultaine
Chesnut Color
pH = 6.0

| Ratio of anionic/ amphoteric | dl Trial 1 | dl Trial 2 | dl Trial 3 | Average | t vs ALS | Significant at 95% ? |
|---|---|---|---|---|---|---|
| 1:0 | 58.28 | 58.14 | 58.17 | 58.20 | | |
| 10:1 | 60.67 | 60.30 | 60.36 | 60.44 | −31.12 | Yes |
| 8:1 | 65.70 | 65.55 | 65.49 | 65.58 | −232.20 | Yes |
| 6:1 | 61.26 | 60.85 | 60.96 | 61.02 | −35.30 | Yes |
| 5:1 | 59.92 | 60.35 | 60.49 | 60.25 | −9.76 | Yes |

As shown in Tables 3–7 and FIGS. 4–8, a series of aqueous solutions were prepared containing ammonium lauryl sulfate (ALS) at 8.55% by weight and cocamidopropylhydroxysultaine (Varion CAS). The ALS was held at a contant level of 8.55 weight percent of the solution while the amount of sultaine was varied from 0.855 to 8.55 weight percent to provide a ratio of ALS:-sultaine ranging from 10:1 to 1:1. Additionally two other solutions were prepared, an 8.55 weight percent of ALS alone in water and an 8.55 weight percent of sultaine alone in water providing the ratios 1:0 and 0:1 respectively. To each solution a quantity of nitrophenylenediamine dyes was added according to the color desired, as shown in Examples 1 and 2:

HAIR COLOR FORMULATION EXAMPLES

| INGREDIENT | 1 wt % | 2 wt % |
|---|---|---|
| 1. Water, soft | qs to 100 | qs to 100 |
| 2. Ammonium Lauryl Sulfate, 30% aqueous solution | 30.0 | 30.0 |
| 3. Varion CAS, 40% aqueous solution | 3.0 | 3.0 |
| 4. N—(2-Hydroxyethyl)-4-nitro-o-phenylenediamine | 0.6 | 0.1 |
| 5. $N^4$—(-2Hydroxyethyl)-2-nitro-p-phenylendiamine | 0.14 | — |
| 6. $N^1,N^4$—bid-(2-Hydroxyethyl)-2-nitro-p-phenylenediamine | 0.075 | 0.03 |
| 7. $N^2,N^4,N^4$—tris-(2-hydroxyethyl)-2-nitro-p-phenylenediamine | 1.6 | 0.6 |
| 8. Citric acid to pH 6.0 ± .1, preservative, fragrance | q.s Chestnut Color | q.s Beige Color |

Figure 8:
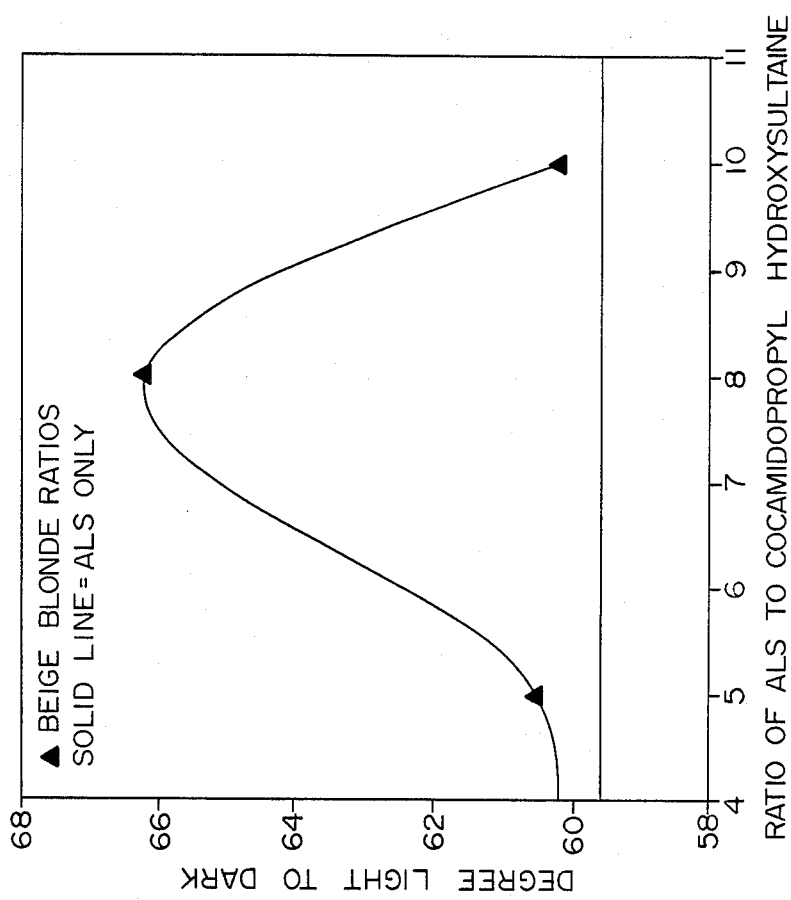
Figure 7:
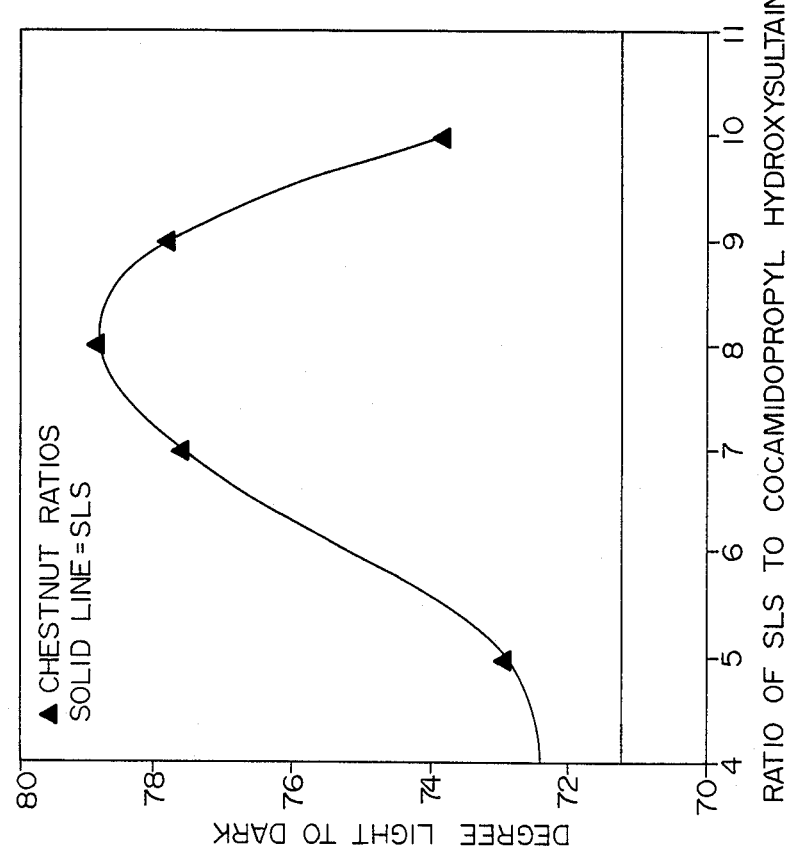

The pH of each solution was adjusted to 6.0±0.1. Best deposition occurred in a 8.55% lauryl sulfate solution, with an 8:1 anionic/amphoteric ratio. Both the 5:1 and 10:1 ratio showed decreased deposition compaared to lauryl sulfate alone, but both the 0.855:1 and 10:1 ratio, at 8.55% lauryl sulfate, were appreciately better at depositing the dye than any 6% or 12% lauryl sulfate solution (compare deposition shown in FIGS. 4, 6 and 7, with dls of 71–79, generally, to the deposition of FIGS. 2 and 3, with dls of 59–65). It should be noted that the dye deposition shown in Table 7 and FIG. 8 is expectedly less since much less dye is included in the composition of Example 2. Analysis of the raw data and graphs show that a 9% by weight lauryl sulfate solution, containing a sultaine, at a lauryl sulfate to sultaine ratio of 6:1 to 9:1 gave dramatic and unexpected increases in dye deposition.

Standard worsted wool all one lot from Test-fabrics, Inc. was used for the evaluation of FIGS. 1–8. A 3"×3" square swatch weighing 2 grams was treated with 2 grams of each dye solution. The dye solution was rubbed in to spread it uniformly over the wool swatch and left on for 15 minutes at room temperature (71°–73° F.). The wool swatch was then rinsed with 100° F. Chicago tap water for 60 seconds. The swatch was allowed to dry overnite. This procedure was repeated three times for each solution. The deposition measurements were made on wool, rather than human hair swatches, since direct dyeing on wool produces more precise and reproducable dye position measurements (better experimental control) than measurements taken from human hair. It is well known that the deposition results obtained on wool are directly related and translatable to deposition achievable on human hair, see Kenny, Commercial Premixed Henna Color Treatments and Conditioners, Cosmetics & Toiletries, Volume 95, page 45.

The color of each swatch was measured using the Mac Beth color eye according to the procedure for measuring wool swatches. The FMC-2 color difference formula was used. Delta L (dl), as reported in Tables 1–7, is the difference in color between an untreated wool swatch and each treated wool swatch. The results were then graphed with Delta L (dl) on the vertical axis and the ratio of anionic detergent to amphoteric surfactant on the horizontal axis. A straight line was drawn at the value of the anionic detergent alone. The student's t-test at 95% confidence was used to indicate which ratios gave a dl significantly different from the anionic alone value. Quite surprisingly, for almost all test solutions, a ratio of anionic lauryl sulfate to amphoteric sultaine in the range of 6:1 to 9:1 gave dramatic and unexpected dye depositions for the nitrophenylenediamine dyes.

TABLE 3 (FIG. 4)

Ammonium Lauryl Sulfate 8.55% Active
Cocamidopropyl Hydroxysultaine
Chestnut Color

| Ratio of anionic/ amphoteric | dl Trial 1 | dl Trial 2 | dl Trial 3 | Average | t vs ALS | Significant at 95% ? |
|---|---|---|---|---|---|---|
| 1:0 | 72.24 | 73.06 | 74.64 | 73.31 | — | — |
| 10:1 | 72.35 | 72.97 | 71.40 | 72.24 | 0.99 | No |
| 9:1 | 77.92 | 77.38 | 77.39 | 77.39 | −5.02 | Yes |
| 8:1 | 78.52 | 78.70 | 78.87 | 78.77 | −8.89 | Yes |
| 7:1 | 78.65 | 78.76 | 78.66 | 78.69 | −7.59 | Yes |
| 6:1 | 76.92 | 76.95 | 76.87 | 76.75 | −4.99 | Yes |
| 5:1 | 71.16 | 70.81 | 73.50 | 71.82 | 3.91 | No |
| 3:1 | 71.65 | 70.89 | 71.10 | 71.21 | 2.46 | No |
| 1:1 | 74.02 | 74.26 | 74.11 | 74.13 | −1.00 | No |
| 0:1 | 73.96 | 73.46 | 74.05 | 73.82 | −0.76 | No |

TABLE 4 (FIG. 5)

Ammonium Lauryl Sulfate 8.55% Active
Cocamidopropyl Betaine
Chestnut Color

| Ratio of anionic/ amphoteric | dl Trial 1 | dl Trial 2 | dl Trial 3 | Average | t vs ALS | Significant at 95% ? |
|---|---|---|---|---|---|---|
| 1:0 | 72.24 | 73.06 | 74.64 | 73.31 | — | — |
| 10:1 | 72.94 | 71.96 | 72.60 | 72.50 | 1.01 | No |
| 8:1 | 72.23 | 72.28 | 73.15 | 72.55 | 1.78 | No |
| 5:1 | 72.13 | 71.09 | 71.81 | 71.68 | 1.00 | No |
| 2:1 | 74.61 | 74.96 | 75.34 | 74.97 | −3.33 | No |
| 1:1 | 71.02 | 71.23 | 71.99 | 71.41 | 4.59 | Yes* |

TABLE 4 (FIG. 5)-continued

Ammonium Lauryl Sulfate 8.55% Active
Cocamidopropyl Betaine
Chestnut Color

| Ratio of anionic/ amphoteric | dl Trial 1 | dl Trial 2 | dl Trial 3 | Average | t vs ALS | Significant at 95% ? |
|---|---|---|---|---|---|---|
| 0:1 | 73.98 | 73.37 | 73.49 | 73.61 | −3.60 | No |

*This result shows that there is significantly less deposition of color with the cocamidopropyl betaine alone compared to the ALS alone.

TABLE 5 (FIG. 6)

Ammonium Lauryl Sulfate 8.55% Active
Cocosultaine
Chestnut Color

| Ratio of anionic/ amphoteric | dl Trial 1 | dl Trial 2 | dl Trial 3 | Average | t vs ALS | Significant at 95% ? |
|---|---|---|---|---|---|---|
| 1:0 | 72.24 | 73.06 | 74.64 | 73.31 | — | — |
| 10:1 | 72.79 | 72.32 | 73.05 | 72.72 | 0.95 | No |
| 8:1 | 78.94 | 78.91 | 78.72 | 78.86 | −7.18 | Yes |
| 5:1 | 71.99 | 72.09 | 73.12 | 72.40 | −0.99 | No |
| 1:1 | 75.73 | 76.72 | 75.83 | 76.09 | −3.49 | No |
| 0:1 | 69.14 | 69.06 | 69.89 | 69.36 | 8.28 | Yes* |

*This result shows that there is significantly less deposition of color with the cocosultaine alone compared to the ALS alone.

TABLE 6 (FIG. 7)

Sodium Lauryl Sulfate 8.55% Active
Cocamidopropyl Hydroxysultaine
Chestnut Color

| Ratio of anionic/ amphoteric | dl Trial 1 | dl Trial 2 | dl Trial 3 | Average | t vs ALS | Significant at 95% ? |
|---|---|---|---|---|---|---|
| 1:0 | 70.36 | 71.23 | 71.86 | 71.15 | — | — |
| 10:1 | 73.79 | 74.19 | 73.39 | 73.78 | −4.52 | Yes |
| 9:1 | 77.84 | 77.75 | 77.76 | 77.78 | −14.43 | Yes |
| 8:1 | 78.66 | 78.83 | 78.98 | 78.82 | −22.40 | Yes |
| 7:1 | 77.67 | 77.74 | 77.48 | 77.63 | −13.28 | Yes |
| 5:1 | 73.60 | 73.46 | 72.86 | 73.30 | −3.32 | No |

*The result for ALS alone is believed to be low, therefore the CAS alone result seems to be significantly higher.

TABLE 7 (FIG. 8)

Ammonium Lauryl Sulfate 8.55% Active
Cocamidopropyl Hydroxysultaine
Beige Blonde Color

| Ratio of anionic/ amphoteric | dl Trial 1 | dl Trial 2 | dl Trial 3 | Average | t vs ALS | Significant at 95% ? |
|---|---|---|---|---|---|---|
| 1:0 | 59.41 | 59.36 | 59.91 | 59.56 | — | — |
| 10:1 | 58.95 | 61.71 | 60.02 | 60.22 | −0.77 | No |
| 8:1 | 66.18 | 66.30 | 66.12 | 66.12 | −30.10 | Yes |
| 5:1 | 61.11 | 59.86 | 60.42 | 60.46 | −2.27 | No |

Figure 4:
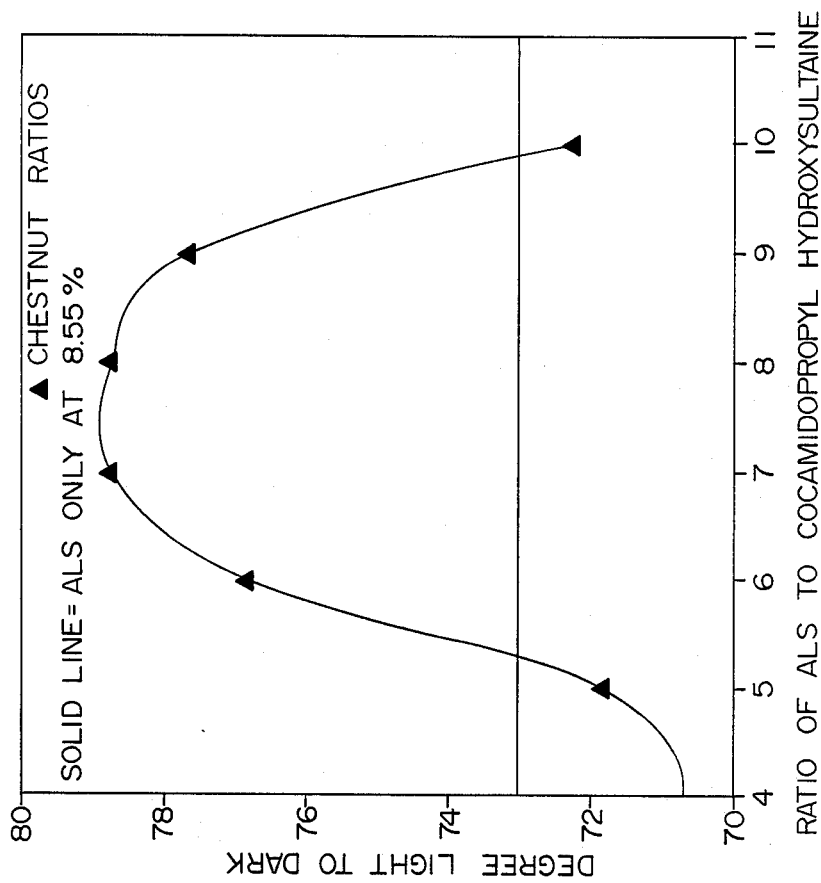
FIGS. 4 and 6–8 are graphs showing color deposition of the nitrophenylenediamine dye compositions of Examples 1 and 2 at various ratios of sulfate/sultaine surfactants.

The values indicated in Tables 1-7 have been graphed as shown in FIGS. 2-8, respectively. The data appearing as dl are numbers representing units of difference in lightness between the untreated sample and a trial. While this quantity is normally indicated as positive if the trial is lighter than the standard and negative if it is darker, the trial in this case is always darker than the standard so that the negative signs have been removed. Thus, for example, in Table 3, as shown in FIG. 4, it is seen that the ratios of anionic/amphoteric in a range of 6:1 to 9:1 provide significantly more darkness to the sample than compositions having anionic/amphoteric ratios outside of this range. In fact, the combination of the anionic and amphoteric in ranges of 3:1; 5:1; and 10:1 provide less dye deposition than the use of the anionic lauryl sulfate alone, otherwise using the formulation of Example 1.

Figure 5:
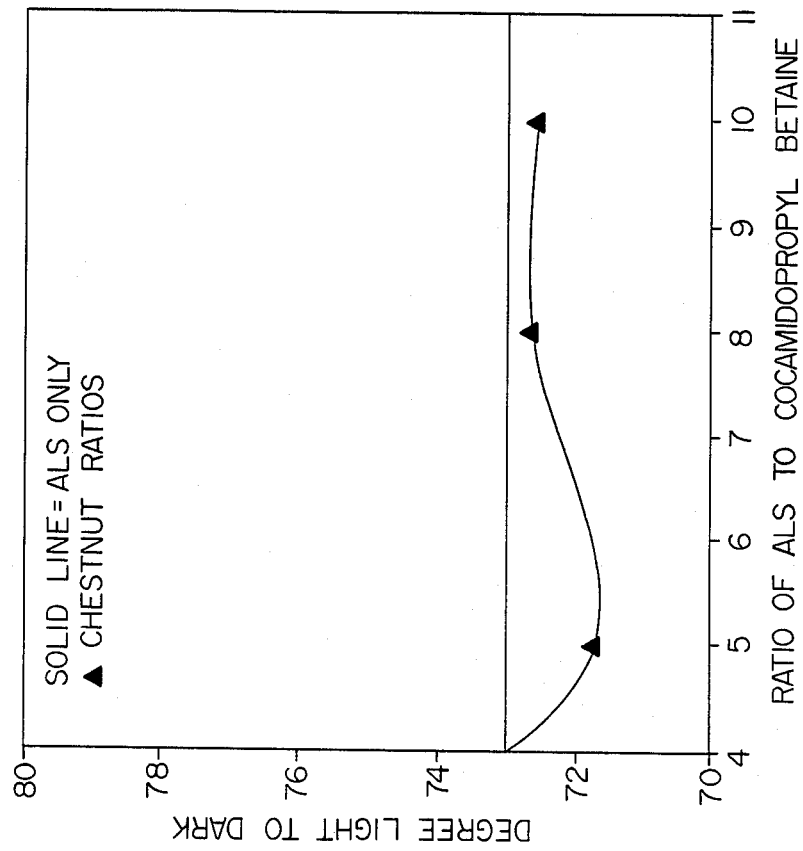
FIG. 5 is a graph showing ineffective color deposition of the dye composition of Example 1, using cocamidopropyl betaine instead of a sultaine, at all ratios of sulfate/betaine above about 4:1.

As shown in Table 4 and FIG. 5, the use of a betaine instead of a sultaine (sulfobetaine) otherwise the composition being the same as that shown in Example 1, provides no ratio of anionic/amphoteric providing as good dye deposition as the use of the lauryl sulfate alone.

Table 5 and FIG. 6 again illustrate the new and unexpected deposition results achieved in accordance with the present invention when the ratio of anionic/amphoteric surfactants are in the range of about 5:1 to about 10:1 provided that the amphoteric is a sultaine (sulfobetaine) used for the deposition of nitrophenylenediamine dyes. Once again, the use of a sultaine alone without the anionic alkyl sulfate, produces significantly less dye deposition than the lauryl sulfate alone; and, ratios of lauryl sulfate/sultaine of less than about 5.5 to 1 or greater than about 9.8 to 1 again produce significantly less dye deposition than the anionic detergent alone. Similar results are shown in Table 6 and FIG. 7 again using the chestnut color of Example 1, but using sodium lauryl sulfate instead of ammonium lauryl sulfate to achieve approximately the same results to achieve significantly better results over the full range of 1:1 to 10:1 sulfate/sultaine.

Table 7 and FIG. 8 show significantly better results for the deposition of the beige blonde nitrophenylenediamine dye mixture of Example 2 (beige blonde) over the fully tested range of 5:1 to 10:1 sulfate/sultaine, although the absolute values of dye deposition only was in the dl 60 to 66+ range compared to values for the dye composition of Example 1 (chestnut color) in the range of dl 71-79. This lower absolute value of dye deposition (although significantly more deposition than the ALS alone) is due to the much lower concentration of nitrophenylenediamine dye in the compositions of Example 2 than the dye concentration in Example 1.

Additional testing was performed on an anthraquinone (Disperse Blue 1) having the following structural formula:

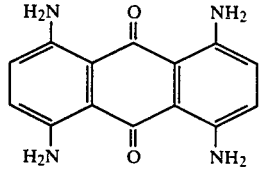

to determine if this combination of an anionic sulphate with a sultaine would be effective for deposition of other types of dyes other than the nitrophenylenediamines. Disperse Blue 1 would not deposit either in the ammonium lauryl sulfate solution alone or in a 8:1 ratio of ammonium lauryl sulfate/cocamidopropylhydroxysultaine solution.

It should be noted that addition of a sultaine, at various ratios, to a sodium lauryl ether sulfate-based shampoo did not improve dye deposition. Likewise, if a betaine is added to a lauryl sulfatebased shampoo (FIG. 5), dye deposition decreases.

The compositions of the present invention possess exceptionally desirable qualities, such as the ability to thoroughly cleanse and evenly dye hair, within reasonable time frames, and leave the hair conditioned, being easier to comb with less fly-away.

It should be understood that the present disclosure has been made only by way of preferred embodiment and that numerous changes in details of construction, combination and arrangement of parts may be resorted to without departing from the spirit and scope of the invention as herein under claimed.

What is claimed and sought to be secured by Letters Patent of the United States is:

1. A semi-permanent hair dye-shampoo composition comprising a tinctorially effective amount of a nitrophenylenediamine semi-permanent dye; a non-ethoxylated water-soluble anionic alkyl sulfate detergent having a formula $C_nH_{2n+1}OSO_3^-M^+$, wherein n a mixture of $=8$ to 18 and M is any suitable cation; and a sultaine surfactant wherein the weight ratios of alkyl sulfate/sultaine is 5.5:1 to 9.8:1 in a suitable carrier.

2. The composition of claim 1 wherein the composition has a pH of 3.0 to 7.0.

3. The composition of claim 1, wherein the sultaine surfactant is a cocoamidosultaine.

4. The composition of claim 3 wherein the cocoamidosultaine is cocamidopropylhydroxysultaine.

5. The composition of claim 1 wherein the sulfate is present in an amount of 6% to 9% by weight of the composition.

6. The composition of claim 5 wherein the sulfate is present in an amount of 8.5% to 9.5% by weight of the composition.

7. The composition of claim 1 wherein the nitrophenylenediamine dye comprises

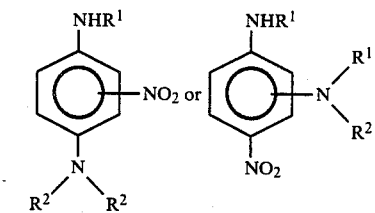

and mixtures thereof, wherein $R^1$, $R^2$, and $R^3$ are the same or different, consisting of hydrogen, methyl, substituted-methyl, ethyl, substituted-ethyl, propyl or substituted propyl moieties and wherein the $NO_2$ and $NR^1R^2$ moieties in formulas I and II are in the ortho or meta positions.

8. The composition of claim 7 wherein the nitrophenylenediamine dyes are one or more wherein $R^1$ or $R^2$ is a monohydroxy lower alkyl radical or an amino lower alkyl radical.

9. The composition of claim 8 wherein the lower alkyl comprises an alkyl having 1-3 carbon atoms.

10. The composition of claim 9 wherein the aminoalkyl radical is an aminodialkyl radical.

11. The composition of claim 7 wherein the nitrophenylenediamine dye is selected from the group consisting of
N-(2-Hydroxyethyl)-4-nitro-o-phenylenediamine; N4-(2-hydroxyethyl)-2-nitro-p-phenylenediamine; N1,N4-bis-(2-hydroxyethyl)-2-nitro-p-phenylenediamine; N2,N4,N4-tris-(2-hydroxyethyl)-2-nitro-p-phenylenediamine; 4-nitro-o-phenylenediamine; 4-nitro-m-phenylenediamine; and mixtures thereof.

12. The composition of claim 1 wherein the carrier comprises water.

13. The composition of claim 1 wherein the sultaine comprises one or more compounds of the formula

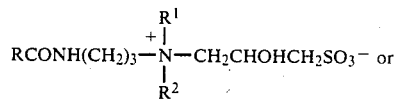

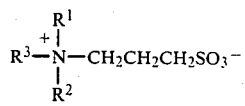

wherein R is an alkyl radical containing predominantly 1 to 17 carbons; $R^1$ and $R^2$ are the same or different alkyl radicals having 1-4 carbons, and $R^3$ is an alkyl radical containing predominantly 8-18 carbons.

14. The composition of claim 13 wherein the sultaine is a hydroxy sultaine.

15. A method of dyeing human hair with a semi-permanent nitrophenylenediamine dye comprising contacting human hair at essentially ambient temperature for a period of time of about 40 minutes or less with a composition comprising a tinctorially effective amount of a nitrophenylenediamine semi-permanent dye; a non-ethoxylated water-soluble anionic alkyl sulfate detergent having a formula $C_nH_{2n+1}OSO_3^-M^+$, wherein n=a mixture of 8 to 18 and M is any suitable cation; and a sultaine surfactant in a suitable carrier wherein the weight ratio of alkyl sulfate sultaine is 5.5:1 to 9.8:1; and thereafter rinsing the hair.

16. The method of claim 15 wherein the sultaine is cocamidopropylhydroxysultaine.

17. The method of claim 15 wherein the sulfate is present in an amount of 6% to 9% by weight of the composition.

18. The method of claim 17 wherein the sulfate is present in an amount of 8.5% to 9.5% by weight of the composition.

19. The method of claim 15 wherein the nitrophenylenediamine dye comprises

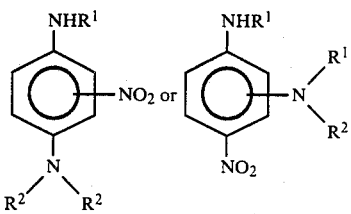

and mixtures thereof, wherein $R^1$, $R^2$, and $R^3$ are the same or different, consisting of hydrogen, methyl, substituted-methyl, ethyl, substituted-ethyl, propyl or substituted propyl moieties.

20. The method of claim 15 wherein the sultaine comprises one or more compounds of the formula

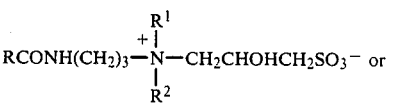

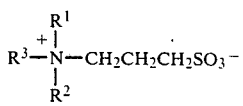

wherein R is an alkyl radical containing predominantly 1 to 17 carbons; $R^1$ and $R^2$ are the same or different alkyl radicals having 1-4 carbons, and $R^3$ is an alkyl radical containing predominantly 8-18 carbons.

21. The method of claim 20 wherein the sultaine is a hydroxy sultaine.

22. The method of claim 20 wherein the is contacted with the nitrophenylene diamine dye for a period of 30 minutes or less.

23. A semi-permanent hair dye-shampoo composition comprising a tinctorially effective amount of a nitrophenylenediamine semi-permanent dye; a non ethoxylated water-soluble anionic alkyl sulfate detergent having a formula $C_nH_{2n+1}OSO_3^-M^+$, wherein n=a mixture of 8 to about 14 and M is any suitable cation; and a sultaine surfactant wherein the weight ratios of alkyl sulfate/sultaine is 5.5:1 to 9.8:1 in a suitable carrier.

24. The composition of claim 23 wherein the composition has a pH of 3.0 to 7.0.

25. The composition of claim 23, wherein the sultaine surfactant is a cocoamidosultiane.

26. The composition of claim 25 wherein the cocoamidosultaine is cocamidopropylhydroxysultaine.

27. The composition of claim 23 wherein the sulfate is present in an amount of 6% to 9% by weight of the composition.

28. The composition of claim 27 wherein the sulfate is present in an amount of 8.5% to 9.5% by weight of the composition.

29. The composition of claim 23 wherein the nitrophenylenediamine dye comprises

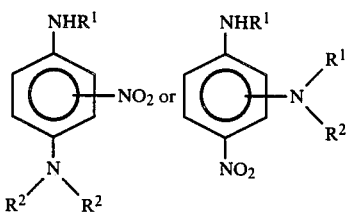

and mixtures thereof, wherein $R^1$, $R^2$, and $R^3$ are the same or different, consisting of hydrogen, methyl, substituted-methyl, ethyl, substituted-ethyl, propyl or substituted propyl moieties and wherein the $NO_2$ and $NR^1R^2$ moities in formulas I and II are in the ortho or meta positions.

30. The composition of claim 29 wherein the nitrophenylenediamine dyes are one or more wherein $R^1$ or $R^2$ is a monohydroxy lower alkyl radical or an amino lower alkyl radical.

31. The composition of claim 30 wherein the lower alkyl comprises an alkyl having 1-3 carbon atoms.

32. The composition of claim 31 wherein the aminoalkyl radical is an aminodialkyl radical.

33. The composition of claim 29 wherein the nitrophenylenediamine dye is selected from the group consisting of N-(2-Hydroxyethyl)-4-nitro-o-phenylenediamine; $N^4$-(2-hydroxyethyl)-2-nitro-p-phenylenediamine; $N^1,N^4$-bis-(2-hydroxyethyl)-2-nitro-p-phenylenediamine; $N^2,N^4,N^4$-tris-(2-hydroxyethyl)-2-nitro-p-phenylenediamine; 4-nitro-o-phenylenediamine; 4-nitro-m-phenylenediamine; and mixtures thereof.

34. The composition of claim 23 wherein the carrier comprises water. comprises one or more compounds of the formula 35. The composition of claim 23 wherein the sultaine

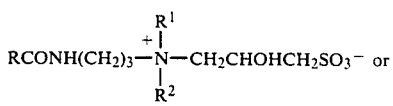

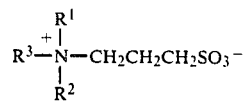

wherein R is an alkyl radical containing predominantly 1 to 17 carbons; $R^1$ and $R^2$ are the same or different alkyl radicals having 1-4 carbons, and $R^3$ is an alkyl radical containing predominantly 8-18 carbons.

36. The composition of claim 35 wherein the sultaine is a hydroxy sultaine.

37. A method of dyeing human hair with a semipermanent nitrophenylenediamine dye comprising contacting human hair at essentially ambient temperature for a period of time of about 40 minutes of less with a composition comprising a tinctorially effective amount of a nitrophenylenediamine semi-permanent dye; a non-ethoxylated water-soluble anionic alkyl sulfate detergent having a formula $C_nH_{2n+1}OSO_3^-M^+$, wherein n=a mixture of 8 to about 12 and M is any suitable cation; and a sultaine surfactant in a suitable carrier wherein the weight ratio of alkyl sulfate sultaine is 5.5:1 to 9.8:1; and thereafter rinsing the hair.

38. The method of claim 37 wherein the sultaine is cocamidopropylhydroxysultaine.

39. The method of claim 37 wherein the sulfate is present in an amount of 6% to 9% by weight of the composition.

40. The method of claim 39 wherein the sulfate is present in an amount of 8.5% to 9.5% by weight of the composition.

41. The method of claim 37 wherein the nitrophenylenediamine dye comprises

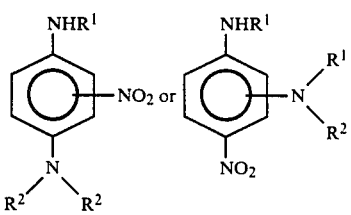

and mixtures thereof, wherein $R^1$, $R^2$, and $R^3$ are the same or different, consisting of hydrogen, methyl, substituted-methyl, ethyl, substituted-ethyl, propyl or substituted propyl moities.

42. The method of claim 37 wherein the sultaine comprises one or more compounds of the formula

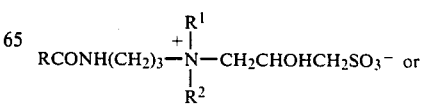

-continued

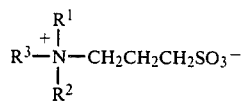

wherein R is an alkyl radical containing predominantly 1 to 17 carbons; $R^1$ and $R^2$ are the same or different alkyl radicals having 1–4 carbons, and $R^3$ is an alkyl radical containing predominantly 8–18 carbons.

43. The method of claim 42 wherein the sultaine is a hydroxy sultaine.

44. The method of claim 42 wherein the hair is contacted with the nitrophenylene diamine dye for a period of 30 minutes or less.

45. A semi-permanent hair dye-shampoo composition comprising a tinctorially effective amount of a nitrophenylenediamine semi-permanent dye; a non-ethoxylated water-soluble anionic alkyl sulfate detergent having a formula $C_nH_{2n+1}OSO_3^-M^+$, wherein $n=12$ and M is any suitable cation; and a sultaine surfactant wherein the weight ratios of alkyl sulfate/sultaine is 5.5:1 to 9.8:1 in a suitable carrier.

46. A method of dyeing human hair with a semi-permanent nitrophenylenediamine dye comprising contacting human hair at essentially ambient temperature for a period of time of about 40 minutes or less with a composition comprising a tinctorially effective amount of a nitrophenylenediamine semi-permanent dye; a non-ethoxylated water-soluble anionic alkyl sulfate detergent having a formula $C_nH_{2n+1}OSO_3^-M^+$, wherein $n=12$ and M is any suitable cation; and a sultaine surfactant in a suitable carrier wherein the weight ratio of alkyl sulfate to sultaine is 5.5:1 to 9.8:1; and thereafter rinsing the hair.

* * * * *